United States Patent
Wang et al.

(10) Patent No.: US 12,046,334 B2
(45) Date of Patent: Jul. 23, 2024

(54) SOURCE IDENTIFICATION FOR UNKNOWN MOLECULES USING MASS SPECTRAL MATCHING

(71) Applicant: The Regents of the University of California, Oakland, CA (US)

(72) Inventors: Mingxun Wang, San Diego, CA (US); Pieter Dorrestein, La Jolla, CA (US); Amina Bouslimani, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 748 days.

(21) Appl. No.: 16/756,711

(22) PCT Filed: Oct. 17, 2018

(86) PCT No.: PCT/US2018/056341
§ 371 (c)(1),
(2) Date: Apr. 16, 2020

(87) PCT Pub. No.: WO2019/079492
PCT Pub. Date: Apr. 25, 2019

(65) Prior Publication Data
US 2020/0265925 A1  Aug. 20, 2020

Related U.S. Application Data
(60) Provisional application No. 62/574,078, filed on Oct. 18, 2017.

(51) Int. Cl.
*G16C 20/20* (2019.01)
*C12Q 1/04* (2006.01)
(Continued)

(52) U.S. Cl.
CPC .............. *G16C 20/20* (2019.02); *C12Q 1/04* (2013.01); *G16C 20/70* (2019.02); *H01J 49/0036* (2013.01)

(58) Field of Classification Search
CPC .......... G16C 20/20; G16C 20/70; C12Q 1/04; H01J 49/0036; H01J 49/04
See application file for complete search history.

(56) References Cited

U.S. PATENT DOCUMENTS

| | | | |
|---|---|---|---|
| 2003/0031350 A1* | 2/2003 | Halpern | H01J 49/0036 382/129 |
| 2004/0096982 A1* | 5/2004 | Barnea | H01J 49/04 436/173 |

(Continued)

FOREIGN PATENT DOCUMENTS

| | | | | |
|---|---|---|---|---|
| CN | 106570351 | * | 4/2014 | ............ G16B 30/00 |
| WO | WO-2004008371 A1 | * | 1/2004 | ......... G01N 33/6848 |

OTHER PUBLICATIONS

Paul Sabatier "A free interactive spectrum analyser" IRAP; 2 Modules 2.1 Spectrum Manager and ASCII parser, 202 Spectrum Analysis, pp. 1-6, pp. 1-2 (Year: 2017).*

(Continued)

*Primary Examiner* — Michael J Dalbo
*Assistant Examiner* — Kaleria Knox
(74) *Attorney, Agent, or Firm* — SCHWEGMAN LUNDBERG & WOESSNER, P.A.

(57) ABSTRACT

Source identification for unknown molecules using mass spectral matching. In an embodiment, a representation of a query mass spectrum is received in a spectrum query. A repository is searched for the query mass spectrum by, for each of a plurality of reference mass spectra, generating a similarity score between the representation of the query mass spectrum and the representation of the reference mass spectrum, when the similarity score exceeds a predeter- (Continued)

mined threshold value, without utilizing a molecular identity of a molecule represented by the reference mass spectrum, retrieving metadata associated with the reference mass spectrum, and derive context information from the retrieved metadata, and adding the context information to consensus metadata associated with the query mass spectrum, wherein the context information indicates a source of the reference mass spectrum. The consensus metadata is then returned in response to the spectrum query.

20 Claims, 8 Drawing Sheets

(51) Int. Cl.
*G16C 20/70* (2019.01)
*H01J 49/00* (2006.01)

(56) References Cited

U.S. PATENT DOCUMENTS

| | | | | |
|---|---|---|---|---|
| 2009/0210194 | A1* | 8/2009 | Ritter | G01N 21/35 356/402 |
| 2011/0202282 | A1* | 8/2011 | Kostrzewa | G16B 50/00 702/19 |
| 2011/0300552 | A1* | 12/2011 | Demirev | C12Q 1/18 204/461 |
| 2014/0297201 | A1* | 10/2014 | Knorr | G01N 30/8693 702/28 |
| 2014/0343864 | A1* | 11/2014 | Strubel | G01N 33/6848 702/19 |
| 2015/0039421 | A1* | 2/2015 | Ford | G06Q 30/0269 705/14.49 |
| 2015/0148242 | A1* | 5/2015 | Magarvey | G16B 20/50 506/8 |
| 2015/0340216 | A1* | 11/2015 | Kwiecien | G06K 9/00543 250/282 |

OTHER PUBLICATIONS

"International Application Serial No. PCT/US2018/056341, International Search Report dated Jan. 4, 2019", 3 pgs.

"International Application Serial No. PCT/US2018/056341, Written Opinion dated Jan. 4, 2019", 5 pgs.

Frank, Ari M, et al., "Clustering Millions of Tandem Mass Spectra", J Proteome Res., 7(1): 113-122, (Jan. 2008), 20 pgs.

Stein, Stephen E, et al., "Optimization and Testing of Mass Spectral Library Search Algorithms for Compound Identification", J Am Soc Mass Spectrom 1994, 5, 859-866, (1994), 8 pgs.

Wang, Mingxun, et al., "Sharing and community curation of mass spectrometry data with GNPS", Nat Biotechnol., 34(8): 828-837, (Aug. 9, 2016), 34 pgs.

Watrous, Jeramie, et al., "Mass spectral molecular networking of living microbial colonies", Proceedings of the National Academy of Sciences, 109(26), E1743-E1752, (May 14, 2012), 10 pgs.

* cited by examiner

SOURCE IDENTIFICATION FOR UNKNOWN MOLECULES USING MASS SPECTRAL MATCHING

CROSS-REFERENCE TO RELATED APPLICATIONS

This application is a U.S. National Stage Filing under 35 U.S.C. 371 from International Application No. PCT/US2018/056341 filed on Oct. 17, 2018, and published as WO 2019/079492 A1 on Apr. 25, 2019, which claims priority to U.S. Provisional Patent App. No. 62/574,078, filed on Oct. 18, 2017, the entirety of each of which is hereby incorporated herein by reference.

BACKGROUND

Field of the Invention

The embodiments described herein are generally directed to mass spectrometry, and, more particularly, to identifying a context for an unknown molecule, based on the mass spectrum for that molecule, without having to identify the molecule itself, and optionally, to model an entire sample based on the identified contexts of its constituent molecules.

Description of the Related Art

Mass spectrometry is a key analytical technology for detecting and identifying small biomolecules, such as peptides, metabolites, and the like. It is orders of magnitude more sensitive than nuclear magnetic resonance (NMR). Tandem mass spectrometry ("MS/MS") refers to a technique that utilizes multiple steps of mass spectrometry to break down a sample into precursor ions, which are then selected for fragmentation into product ions. The result is an MS/MS spectrum (simply referred to herein, along with other types of mass spectrum, as a "spectrum") of the fragments, which can be used to reveal aspects of the chemical structure of the precursor ions, and thereby the sample. In general, a spectrum will comprise a set of mass and intensity pairs, called "peaks," that may be assigned into uniformly sized mass bins. However, it should be understood that, as used herein, a spectrum may be defined in any manner as long as it provides a signature or "fingerprint" of a molecule's mass.

Using conventional systems, a user may compare a spectrum for an unknown molecule to spectra, stored in a spectral library, for which molecules have been previously identified. In this manner, users can identify known molecules whose spectra match the spectrum of their unknown molecules, and utilize the identity of their now known molecules to obtain additional information about their molecules. However, these conventional systems require the molecules in the library to have been previously identified.

What is needed is a system that can provide information which can be used to identify the source of a particular molecule, based on its spectrum, even when that molecule has not been previously identified in a spectral library.

SUMMARY

Accordingly, systems, methods, and non-transitory computer-readable media are disclosed to identify a context for an unknown molecule, based on the mass spectrum for that molecule, without having to identify the molecule itself, and optionally, to model an entire sample based on the contexts of its constituent molecules. Advantageously, these contexts and models can be used to identify the unknown molecule's source, even when the molecule has not been previously identified in a repository of spectra. Furthermore, since the repository of searchable spectra is no longer restricted to only previously identified spectra, disclosed embodiments enable a vast new universe of information.

In an embodiment, a method is disclosed that comprises using at least one hardware processor to: receive a spectrum query comprising a representation of a query mass spectrum of a molecule; search a repository for the query mass spectrum by, for each of a first plurality of representations of reference mass spectra in the repository, generating a similarity score between the representation of the query mass spectrum and the representation of the reference mass spectrum, when the similarity score exceeds a predetermined threshold value, without utilizing a molecular identity of a molecule represented by the reference mass spectrum, retrieving metadata associated with the reference mass spectrum, and derive context information from the retrieved metadata, and adding the context information to consensus metadata associated with the query mass spectrum, wherein the context information indicates a source of the reference mass spectrum; and return the consensus metadata, including the context information, in response to the spectrum query. The method may further comprise using the at least one hardware processor to: store a second plurality of representations of reference mass spectra in the repository; cluster the second plurality of representations of reference mass spectra into a plurality of clusters; and generate the first plurality of representations of reference mass spectra to be used in the search of the repository by, for each of the plurality of clusters, generating a representation of a reference mass spectrum that represents all representations of reference mass spectra within that cluster. Generating a similarity score between the representation of the query mass spectrum and the representation of the reference mass spectrum may comprise computing a cosine of an angle between a vector representation of the query mass spectrum and a vector representation of the reference mass spectrum, and/or computing a shared peak count between the query mass spectrum and the reference mass spectrum. The query mass spectrum and each of the reference mass spectra may be generated using tandem mass spectrometry. The first plurality of representations of reference mass spectra used in the search may be at least a subset of a second plurality of representations of reference mass spectra in the repository, wherein the method further comprises using the at least one hardware processor to store the second plurality of representations of reference mass spectra in the repository in a plurality of datasets, and wherein each dataset represents a single context, such that each of the representations of reference mass spectra within each dataset represents a molecule obtained within the single context of that dataset. Each of the plurality of datasets may comprise a plurality of spectra samples, wherein each of the plurality of spectra samples in each dataset comprises one or more of the second plurality of representations of reference mass spectra that represent a molecule obtained from a single sample within the single context of that dataset. Each of the plurality of spectra samples in each of the plurality of datasets may be associated with sample-specific metadata, and the retrieved metadata associated with a reference mass spectrum may comprise the sample-specific metadata associated with the spectra sample that comprises a representation of the reference mass spectrum. When the similarity scores between the representation of the query mass spectrum and two or more of the first plurality of representations of reference mass spectra within the same dataset all exceed the predetermined threshold value, only the context information, from the metadata associated with one of the two or more representations of reference mass spectra having the highest similarity score, may be added to the consensus metadata. Each of the plurality of datasets may be associated with dataset-specific metadata, and the retrieved metadata associated with a reference mass spectrum may comprise the dataset-specific metadata associated with the dataset that comprises a representation of the reference mass spectrum. The context information in the consensus metadata may indicate a plurality of distinct sources. The spectrum query may comprise one or more filters, and the search may be restricted in accordance with the one or more filters. The one or more filters may comprise a window filter that restricts the search to a window that represents only a portion of the query mass spectrum. The one or more filters may comprise a precursor filter that removes peaks around a precursor peak within a window that represents only a portion of the query mass spectrum. The method may further comprise using the at least one hardware processor to, for each of the first plurality of representations of reference mass spectra in the repository, when the similarity score exceeds the predetermined threshold value and when the retrieved metadata associated with the reference spectrum comprises the molecular identity of the molecule represented by the reference mass spectrum, add the molecular identity of the molecule represented by the reference mass spectrum to the consensus metadata associated with the query mass spectrum. The method may further comprise using the at least one hardware processor to: receive a sample query comprising a representation of a sample, wherein the representation of the sample comprises a plurality of representations of query mass spectra of molecules within the sample; and generate a spectrum query and search the repository for each of the plurality of query mass spectra to generate consensus metadata that includes context information for all of the query mass spectra. The method may further comprise using the at least one hardware processor to: identify at least one approximate mass spectrum that differs by a mass tolerance from the query mass spectrum; and search the repository for the at least one approximate mass spectrum by, for each of the first plurality of representations of reference mass spectra in the repository, generating a similarity score between a representation of the approximate mass spectrum and the representation of the reference mass spectrum, when the similarity score exceeds a predetermined threshold value, without utilizing a molecular identity of a molecule represented by the reference mass spectrum, retrieving metadata associated with the reference mass spectrum, and derive context information from the retrieved metadata, and adding the context information to the consensus metadata, wherein the context information indicates a source of the reference mass spectrum. The method may be embodied in executable software modules of a processor-based system, such as a server, and/or in executable instructions stored in a non-transitory computer-readable medium.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

In an embodiment, systems, methods, and non-transitory computer-readable media are disclosed to identify a context for an unknown molecule, based on the mass spectrum for that molecule, without having to identify the molecule itself, and optionally, to model an entire sample based on the contexts of its constituent molecules. After reading this description, it will become apparent to one skilled in the art how to implement the invention in various alternative embodiments and alternative applications. However, although various embodiments of the present invention will be described herein, it is understood that these embodiments are presented by way of example and illustration only, and not limitation. As such, this detailed description of various embodiments should not be construed to limit the scope or breadth of the present invention as set forth in the appended claims.

1. System Overview 1.1. Infrastructure

Figure 1:
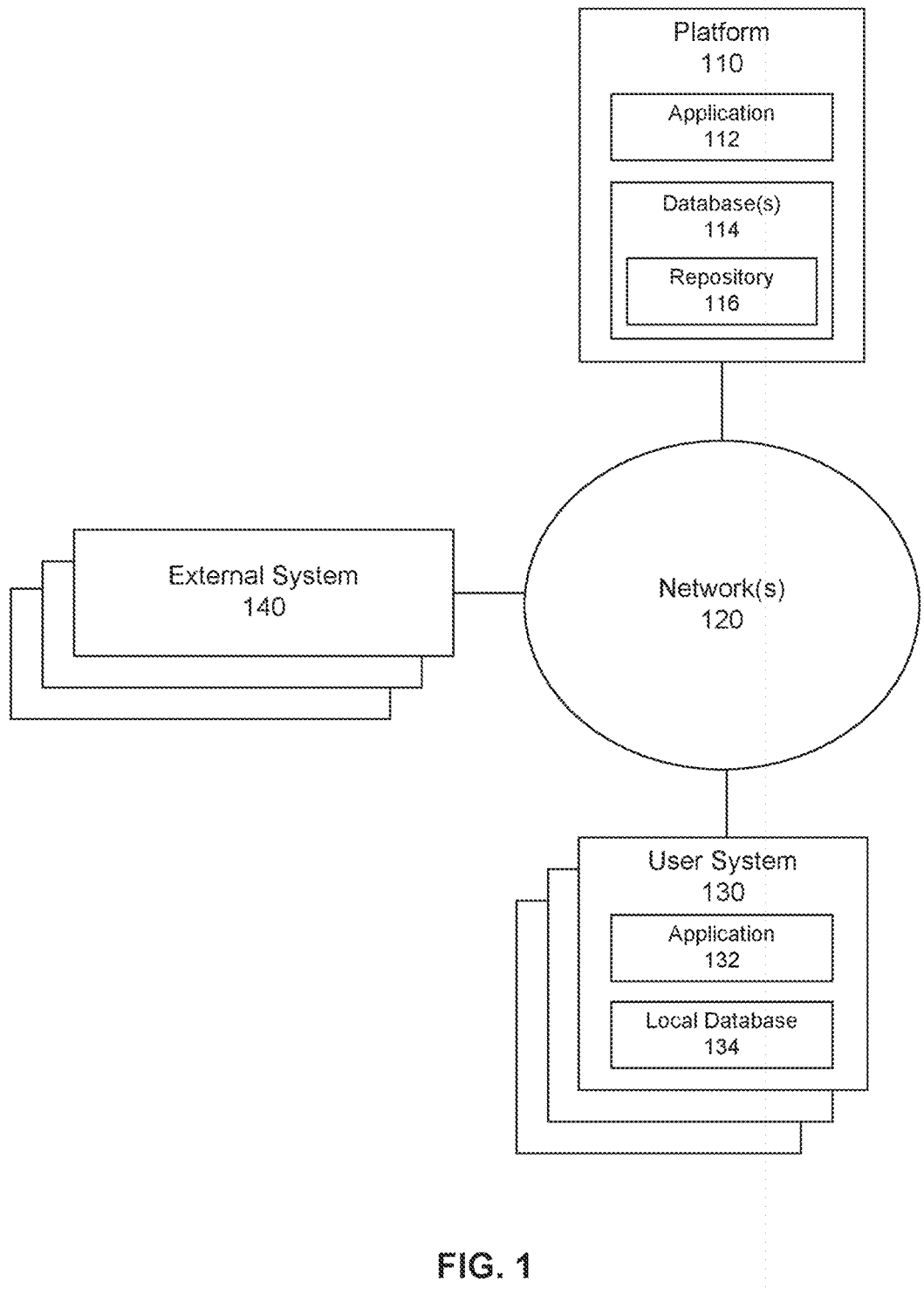
FIG. 1 illustrates an example infrastructure, in which one or more of the processes described herein, may be implemented, according to an embodiment.

FIG. 1 is a block diagram illustrating an example infrastructure, in which one or more of the disclosed processes may operate, according to an embodiment. The infrastructure may comprise a platform 110 (e.g., one or more servers) which hosts and/or executes one or more of the various functions, processes, methods, and/or software modules described herein. Platform 110 may comprise dedicated servers, or may instead comprise cloud instances, which utilize shared resources of one or more servers. These servers or cloud instances may be collocated and/or geographically distributed. Platform 110 may also comprise or be communicatively connected to a server application 112 and/or one or more databases 114. In addition, platform 110 may be communicatively connected to one or more user systems 130 via one or more networks 120. Platform 110 may also be communicatively connected to one or more external systems 140 (e.g., other platforms, websites, etc.) via one or more networks 120.

Network(s) 120 may comprise the Internet, and platform 110 may communicate with user system(s) 130 through the Internet using standard transmission protocols, such as HyperText Transfer Protocol (HTTP), HTTP Secure (HTTPS), File Transfer Protocol (FTP), FTP Secure (FTPS), Secure Shell FTP (SFTP), and the like, as well as proprietary protocols. While platform 110 is illustrated as being connected to various systems through a single set of network(s) 120, it should be understood that platform 110 may be connected to the various systems via different sets of one or more networks. For example, platform 110 may be connected to a subset of user systems 130 and/or external systems 140 via the Internet, but may be connected to one or more other user systems 130 and/or external systems 140 via an intranet. Furthermore, while only a few user systems 130 and external systems 140, one server application 112, and one set of database(s) 114 are illustrated, it should be understood that the infrastructure may comprise any number of user systems, external systems, server applications, and databases.

User system(s) 130 may comprise any type or types of computing devices capable of wired and/or wireless communication, including without limitation, desktop computers, laptop computers, tablet computers, smart phones or other mobile phones, servers, televisions, set-top boxes, electronic kiosks, point-of-sale terminals, and/or the like.

Platform 110 may comprise web servers which host one or more websites and/or web services. In embodiments in which a website is provided, the website may comprise a graphical user interface, including, for example, one or more screens (e.g., webpages) generated in HyperText Markup Language (HTML) or other language. Platform 110 transmits or serves one or more screens of the graphical user interface in response to requests from user system(s) 130. In some embodiments, these screens may be served in the form of a wizard, in which case two or more screens may be served in a sequential manner, and one or more of the sequential screens may depend on an interaction of the user or user system 130 with one or more preceding screens. The requests to platform 110 and the responses from platform 110, including the screens of the graphical user interface, may both be communicated through network(s) 120, which may include the Internet, using standard communication protocols (e.g., HTTP, HTTPS, etc.). These screens (e.g., webpages) may comprise a combination of content and elements, such as text, images, videos, animations, references (e.g., hyperlinks), frames, inputs (e.g., textboxes, text areas, checkboxes, radio buttons, drop-down menus, buttons, forms, etc.), scripts (e.g., JavaScript), and the like, including elements comprising or derived from data stored in one or more databases (e.g., database(s) 114) that are locally and/or remotely accessible to platform 110. Platform 110 may also respond to other requests from user system(s) 130.

Platform 110 may further comprise, be communicatively coupled with, or otherwise have access to one or more database(s) 114. For example, platform 110 may comprise one or more database servers which manage one or more databases 114. Database(s) 114 may comprise the repository 116 described elsewhere herein. A user system 130 or server application 112 executing on platform 110 may submit data (e.g., user data, form data, etc.) to be stored in database(s) 114, and/or request access to data stored in database(s) 114. Any suitable database may be utilized, including without limitation MySQL™, Oracle™ IBM™, Microsoft SQL™, Access™, and the like, including cloud-based databases and proprietary databases. Data may be sent to platform 110, for instance, using the well-known POST request supported by HTTP, via FTP, and/or the like. This data, as well as other requests, may be handled, for example, by server-side web technology, such as a servlet or other software module (e.g., comprised in server application 112), executed by platform 110.

In embodiments in which a web service is provided, platform 110 may receive requests from external system(s) 140, and provide responses in eXtensible Markup Language (XML), JavaScript Object Notation (JSON), and/or any other suitable or desired format. In such embodiments, platform 110 may provide an application programming interface (API) which defines the manner in which user system(s) 130 and/or external system(s) 140 may interact with the web service. Thus, user system(s) 130 and/or external system(s) 140 (which may themselves be servers), can define their own user interfaces, and rely on the web service to implement or otherwise provide the backend processes, methods, functionality, storage, and/or the like, described herein. For example, in such an embodiment, a client application 132 executing on one or more user system(s) 130 may interact with a server application 112 executing on platform 110 to execute one or more or a portion of one or more of the various functions, processes, methods, and/or software modules described herein. Client application 132 may be "thin," in which case processing is primarily carried out server-side by server application 112 on platform 110. A basic example of a thin client application is a browser application, which simply requests, receives, and renders webpages at user system(s) 130, while the server application on platform 110 is responsible for generating the webpages and managing database functions.

Alternatively, the client application may be "thick," in which case processing is primarily carried out client-side by user system(s) 130. It should be understood that client application 132 may perform an amount of processing, relative to server application 112 on platform 110, at any point along this spectrum between "thin" and "thick," depending on the design goals of the particular implementation. In any case, the application described herein, which may wholly reside on either platform 110 (e.g., in which case server application 112 performs all processing) or user system(s) 130 (e.g., in which case client application 132 performs all processing) or be distributed between platform 110 and user system(s) 130 (e.g., in which case server application 112 and client application 132 both perform processing), can comprise one or more executable software modules that implement one or more of the functions, processes, or methods of the application described herein.

1.2. Example Processing Device

Figure 2:
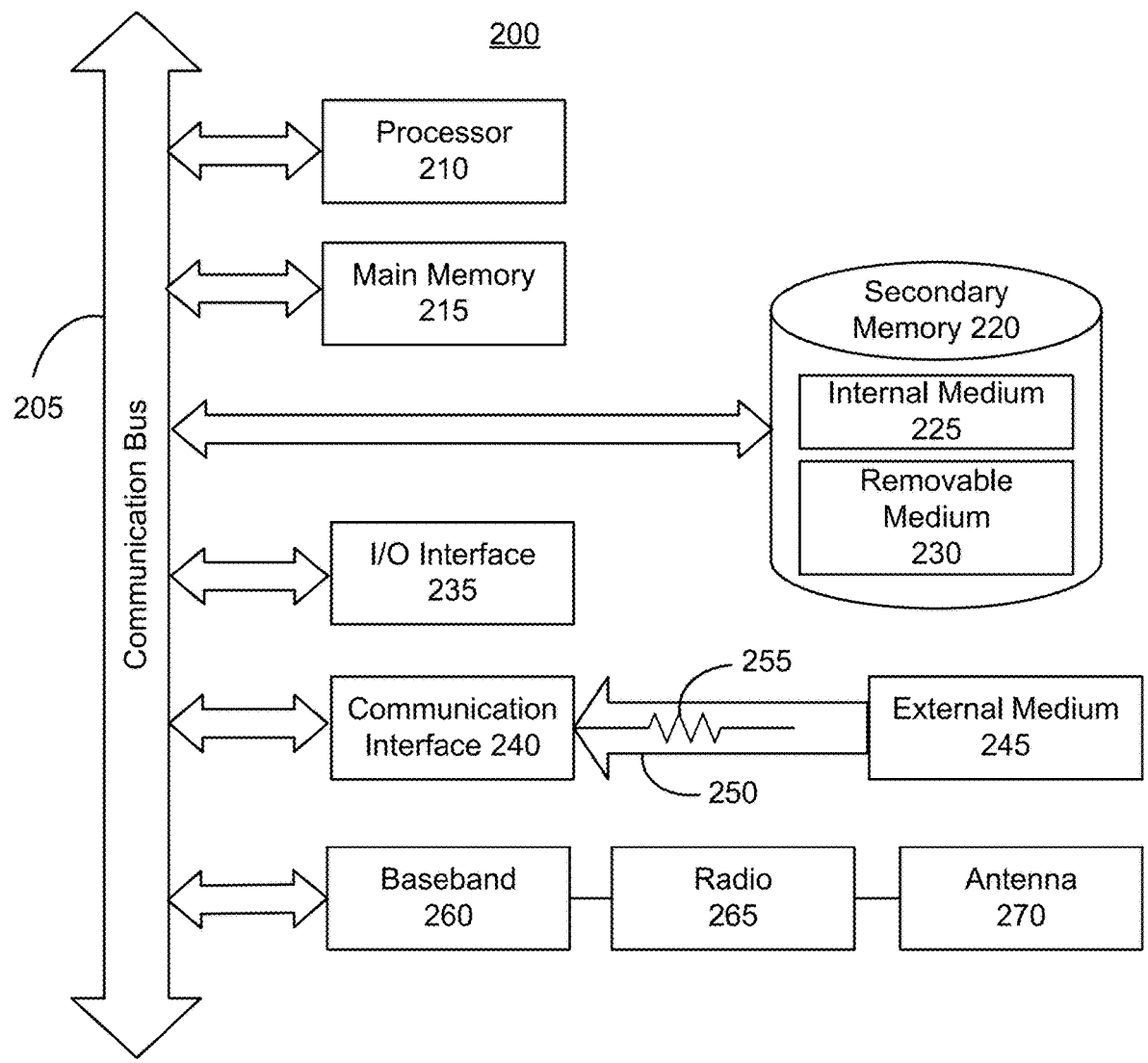
FIG. 2 illustrates an example processing system, by which one or more of the processed described herein, may be executed, according to an embodiment.

FIG. 2 is a block diagram illustrating an example wired or wireless system 200 that may be used in connection with various embodiments described herein. For example, system 200 may be used as or in conjunction with one or more of the functions, processes, or methods (e.g., to store and/or execute the application or one or more software modules of the application) described herein, and may represent components of platform 110, user system(s) 130, external system(s) 140, and/or other processing devices described herein. System 200 can be a server or any conventional personal computer, or any other processor-enabled device that is capable of wired or wireless data communication. Other computer systems and/or architectures may be also used, as will be clear to those skilled in the art.

System 200 preferably includes one or more processors, such as processor 210. Additional processors may be provided, such as an auxiliary processor to manage input/output, an auxiliary processor to perform floating-point mathematical operations, a special-purpose microprocessor having an architecture suitable for fast execution of signal-processing algorithms (e.g., digital-signal processor), a slave processor subordinate to the main processing system (e.g., back-end processor), an additional microprocessor or controller for dual or multiple processor systems, and/or a coprocessor. Such auxiliary processors may be discrete processors or may be integrated with processor 210.

Examples of processors which may be used with system 200 include, without limitation, the Pentium® processor, Core i7® processor, and Xeon® processor, all of which are available from Intel Corporation of Santa Clara, California.

Processor 210 is preferably connected to a communication bus 205. Communication bus 205 may include a data channel for facilitating information transfer between storage and other peripheral components of system 200. Furthermore, communication bus 205 may provide a set of signals used for communication with processor 210, including a data bus, address bus, and/or control bus (not shown). Communication bus 205 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, standards promulgated by the Institute of Electrical and Electronics Engineers (IEEE) including IEEE 488 general-purpose interface bus (GPM), IEEE 696/S-100, and/or the like.

System 200 preferably includes a main memory 215 and may also include a secondary memory 220. Main memory 215 provides storage of instructions and data for programs executing on processor 210, such as one or more of the functions and/or modules discussed herein. It should be understood that programs stored in the memory and executed by processor 210 may be written and/or compiled according to any suitable language, including without limitation C/C++, Java, JavaScript, Perl, Visual Basic, .NET, and the like. Main memory 215 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

Secondary memory 220 may optionally include an internal medium 225 and/or a removable medium 230. Removable medium 230 is read from and/or written to in any well-known manner. Removable storage medium 230 may be, for example, a magnetic tape drive, a compact disc (CD) drive, a digital versatile disc (DVD) drive, other optical drive, a flash memory drive, and/or the like.

Secondary memory 220 is a non-transitory computer-readable medium having computer-executable code (e.g., disclosed software modules) and/or other data stored thereon. The computer software or data stored on secondary memory 220 is read into main memory 215 for execution by processor 210.

In alternative embodiments, secondary memory 220 may include other similar means for allowing computer programs or other data or instructions to be loaded into system 200. Such means may include, for example, a communication interface 240, which allows software and data to be transferred from external storage medium 245 to system 200. Examples of external storage medium 245 may include an external hard disk drive, an external optical drive, an external magneto-optical drive, and/or the like. Other examples of secondary memory 220 may include semiconductor-based memory, such as programmable read-only memory (PROM), erasable programmable read-only memory (EPROM), electrically erasable read-only memory (EEPROM), and flash memory (block-oriented memory similar to EEPROM).

As mentioned above, system 200 may include a communication interface 240. Communication interface 240 allows software and data to be transferred between system 200 and external devices (e.g. printers), networks, or other information sources. For example, computer software or executable code may be transferred to system 200 from a network server (e.g., platform 110) via communication interface 240. Examples of communication interface 240 include a built-in network adapter, network interface card (NIC), Personal Computer Memory Card International Association (PCMCIA) network card, card bus network adapter, wireless network adapter, Universal Serial Bus (USB) network adapter, modem, a wireless data card, a communications port, an infrared interface, an IEEE 1394 fire-wire, and any other device capable of interfacing system 200 with a network (e.g., network(s) 120) or another computing device. Communication interface 240 preferably implements industry-promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 240 are generally in the form of electrical communication signals 255. These signals 255 may be provided to communication interface 240 via a communication channel 250. In an embodiment, communication channel 250 may be a wired or wireless network (e.g., network(s) 120), or any variety of other communication links. Communication channel 250 carries signals 255 and can be implemented using a variety of wired or wireless communication means including wire or cable, fiber optics, conventional phone line, cellular phone link, wireless data communication link, radio frequency ("RF") link, or infrared link, just to name a few.

Computer-executable code (e.g., computer programs, such as the disclosed application, or software modules) is stored in main memory 215 and/or secondary memory 220. Computer programs can also be received via communication interface 240 and stored in main memory 215 and/or secondary memory 220. Such computer programs, when executed, enable system 200 to perform the various functions of the disclosed embodiments as described elsewhere herein.

In this description, the term "computer-readable medium" is used to refer to any non-transitory computer-readable storage media used to provide computer-executable code and/or other data to or within system 200. Examples of such media include main memory 215, secondary memory 220 (including internal memory 225, removable medium 230, and external storage medium 245), and any peripheral device communicatively coupled with communication interface 240 (including a network information server or other network device). These non-transitory computer-readable media are means for providing executable code, programming instructions, software, and/or other data to system 200.

In an embodiment that is implemented using software, the software may be stored on a computer-readable medium and loaded into system 200 by way of removable medium 230, I/O interface 235, or communication interface 240. In such an embodiment, the software is loaded into system 200 in the form of electrical communication signals 255. The software, when executed by processor 210, preferably causes processor 210 to perform one or more of the processes and functions described elsewhere herein.

In an embodiment, I/O interface 235 provides an interface between one or more components of system 200 and one or more input and/or output devices. Example input devices include, without limitation, sensors, keyboards, touch screens or other touch-sensitive devices, biometric sensing devices, computer mice, trackballs, pen-based pointing devices, and/or the like. Examples of output devices include, without limitation, other processing devices, cathode ray tubes (CRTs), plasma displays, light-emitting diode (LED) displays, liquid crystal displays (LCDs), printers, vacuum fluorescent displays (VFDs), surface-conduction electron-emitter displays (SEDs), field emission displays (FEDs), and/or the like. In some cases, an input and output device may be combined, such as in the case of a touch panel display (e.g., in a smartphone, tablet, or other mobile device).

System 200 may also include optional wireless communication components that facilitate wireless communication over a voice network and/or a data network (e.g., in the case of user system 130). The wireless communication components comprise an antenna system 270, a radio system 265, and a baseband system 260. In system 200, radio frequency (RF) signals are transmitted and received over the air by antenna system 270 under the management of radio system 265.

In an embodiment, antenna system 270 may comprise one or more antennae and one or more multiplexors (not shown) that perform a switching function to provide antenna system 270 with transmit and receive signal paths. In the receive path, received RF signals can be coupled from a multiplexor to a low noise amplifier (not shown) that amplifies the received RF signal and sends the amplified signal to radio system 265.

In an alternative embodiment, radio system 265 may comprise one or more radios that are configured to communicate over various frequencies. In an embodiment, radio system 265 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from radio system 265 to baseband system 260.

If the received signal contains audio information, then baseband system 260 decodes the signal and converts it to an analog signal. Then the signal is amplified and sent to a speaker. Baseband system 260 also receives analog audio signals from a microphone. These analog audio signals are converted to digital signals and encoded by baseband system 260. Baseband system 260 also encodes the digital signals for transmission and generates a baseband transmit audio signal that is routed to the modulator portion of radio system 265. The modulator mixes the baseband transmit audio signal with an RF carrier signal, generating an RF transmit signal that is routed to antenna system 270 and may pass through a power amplifier (not shown). The power amplifier amplifies the RF transmit signal and routes it to antenna system 270, where the signal is switched to the antenna port for transmission.

Baseband system 260 is also communicatively coupled with processor 210, which may be a central processing unit (CPU). Processor 210 has access to data storage areas 215 and 220. Processor 210 is preferably configured to execute instructions (i.e., computer programs, such as the disclosed application, or software modules) that can be stored in main memory 215 or secondary memory 220. Computer programs can also be received from baseband processor 260 and stored in main memory 210 or in secondary memory 220, or executed upon receipt. Such computer programs, when executed, enable system 200 to perform the various functions of the disclosed embodiments.

1.3. Example Repository

Figure 3:
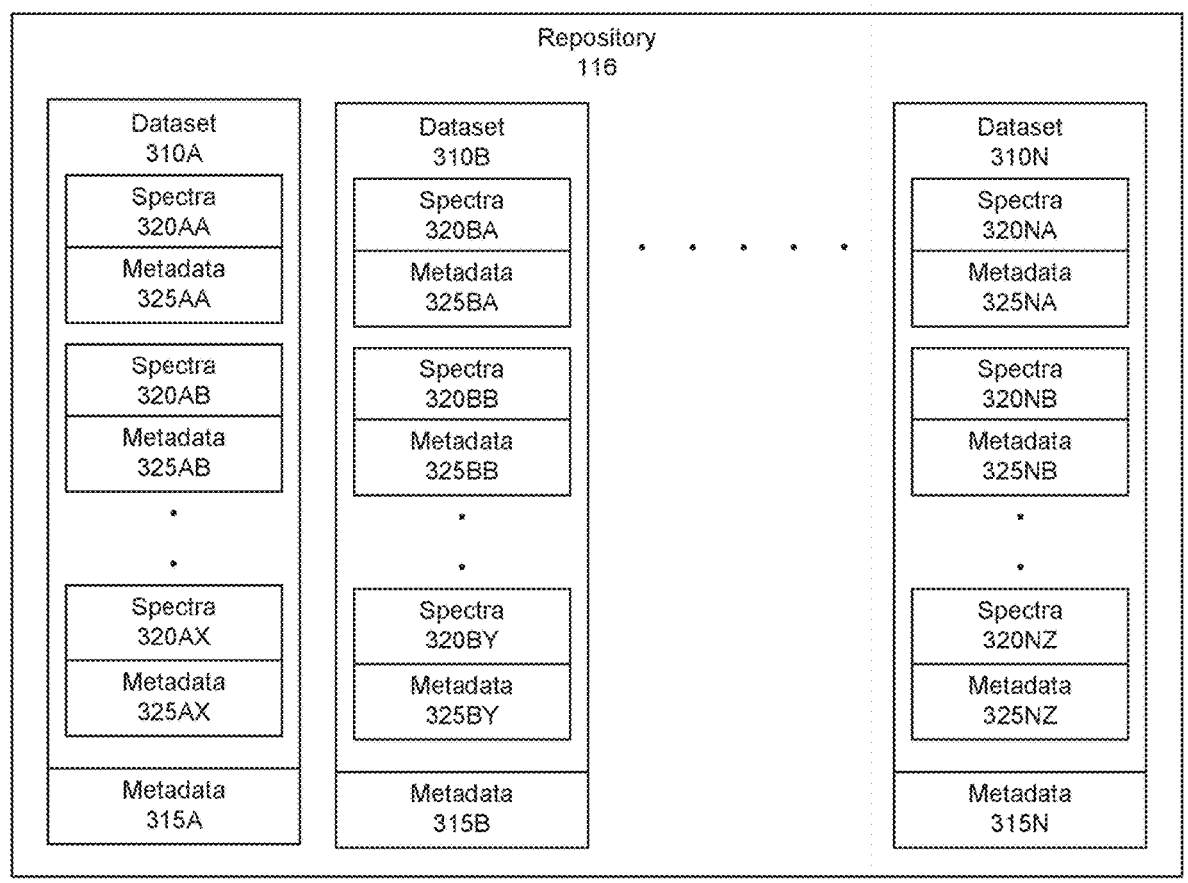
FIG. 3 is a block diagram illustrating an example repository, according to an embodiment.

FIG. 3 is a block diagram illustrating an example repository 116, according to an embodiment. In the illustrated embodiment, repository 116 comprises a plurality of datasets 310. Repository 116 may comprise any number of datasets 310. In addition, repository 116 comprises dataset-specific metadata 315 for each of the plurality of datasets 310. Each set of metadata 315 for a dataset 310 may comprise, without limitation, a title of the dataset 310, a description of the dataset 310, organism(s) from which spectra sample 320 in the dataset 310 were obtained, collector(s) (e.g., user, person, organization, etc.) of the spectra sample 320 in the dataset 310 and/or the metadata 315, and/or the like. However, it is contemplated that each set of metadata 315 may comprise fewer, more, or different fields than those described, and not all fields may be applicable to all datasets 310. Each individual dataset may represent one or more samples from a single respective context (e.g., a single specific organism, a single type of organism, a single clinical study, a single pharmaceutical product, a single line of personal care product, etc.).

In an embodiment, each dataset 310 comprises a plurality of spectra samples 320 (e.g., acquired within the single context of the dataset 310). Each spectra sample 320 represents all of the molecules within a single sample (e.g., biological sample), and will comprise one or more—but generally a plurality (e.g., thousands)—of spectra. Each spectra sample 320 may comprise all of the spectra derived from the corresponding sample, including spectra for unknown molecules with incomplete or no structural information. It should be understood that repository 116 may comprise spectra samples 320 for a vast variety of reference samples. For example, the samples could be from animal products, bodily fluids, foods, personal care products, contaminants, medication formulations, pharmaceutical products, microbial species, building materials, and any other substances for which mass spectrometry (e.g., tandem mass spectrometry) can produce a mass signature. Advantageously, disclosed embodiments are scalable (e.g., using the cluster-based searching described elsewhere herein), such that the size of repository 116 (corresponding to the number of spectra samples 320) is virtually unlimited.

In addition, each spectra sample 320 in the dataset 310 may be associated with sample-specific metadata 325. Each set of metadata 325 for a spectra sample 320 may comprise, without limitation, organism(s) from which the spectra sample 320 was obtained, body site(s) from which the spectra sample 320 was obtained, disease(s) associated with the spectra sample 320, instrument type(s) used to acquire the spectra sample 320, chromatography condition(s) used to acquire the spectra sample 320, gender of the organism(s) from which the spectra sample 320 was obtained, a type of the spectra sample (e.g., stool, urine, blood, etc.), and/or the like. However, it is contemplated that each set of metadata 325 may comprise fewer, more, or different fields than those described, and that not all fields may be applicable to all spectra samples 320.

In an embodiment, each dataset 310 represents a single context. As used herein, the term "context" refers to one or more circumstances forming a shared setting in which all of the biological samples, represented by the spectra samples 320 within the dataset 310, were obtained. For example, a context may be that all of the spectra samples 320 in the dataset 310 were obtained from a specific organism or type of organism, were obtained from a specific location (e.g., a specific site on a specific organism or type of organism), are associated with a specific condition (e.g., a medical condition, such as diabetes), were obtained in the same specific clinical study or experiment (e.g., samples from both diabetic and non-diabetic patients during a study on diabetes), and/or the like. Thus, the context of a particular spectrum may be thought of as the source or origin (e.g., skin sample, pharmaceutical compound, etc.) of that spectrum, and therefore, can be used to infer the source of a similar spectrum. The particular context, represented by a specific dataset 310, is identified or otherwise indicated in the metadata 315 associated with that specific dataset 310. It should be understood that, depending on the context, a dataset 310 may be either heterogeneous or homogeneous. For example, within the context of a specific organism, all of the spectra samples 320 in a dataset 310 represent a sample from that organism, and therefore, the dataset 310 can be considered homogeneous. In contrast, within the context of a clinical study, the spectra samples 320 in a dataset 310 may represent samples from different subjects who may or may not have the medical condition being studied, and therefore, the dataset 310 can be considered heterogeneous.

2. Process Overview

Embodiments of processes for identifying a context for an unknown molecule, based on the mass spectrum for that molecule, without having to identify the molecule itself, and modeling an entire sample based on the contexts of its constituent molecules, will now be described in detail. It should be understood that the described processes may be embodied in one or more software modules that are executed by one or more hardware processors (e.g., processor 210), e.g., as the application discussed herein (e.g., server application 112, client application 132, and/or a distributed application comprising both server application 112 and client application 132), which may be executed wholly by processor(s) of platform 110, wholly by processor(s) of user system(s) 130, or may be distributed across platform 110 and user system(s) 130, such that some portions or modules of the application are executed by platform 110 and other portions or modules of the application are executed by user system(s) 130. The described process may be implemented as instructions represented in source code, object code, and/or machine code. These instructions may be executed directly by the hardware processor(s), or alternatively, may be executed by a virtual machine operating between the object code and the hardware processors. In addition, the disclosed application may be built upon or interfaced with one or more existing systems.

Alternatively, the described processes may be implemented as a hardware component (e.g., general-purpose processor, integrated circuit (IC), application-specific integrated circuit (ASIC), digital signal processor (DSP), field-programmable gate array (FPGA) or other programmable logic device, discrete gate or transistor logic, etc.), combination of hardware components, or combination of hardware and software components. To clearly illustrate the interchangeability of hardware and software, various illustrative components, blocks, modules, circuits, and steps are described herein generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a component, block, module, circuit, or step is for ease of description. Specific functions or steps can be moved from one component, block, module, circuit, or step to another without departing from the invention.

2.1. Searching the Repository

Figure 4:
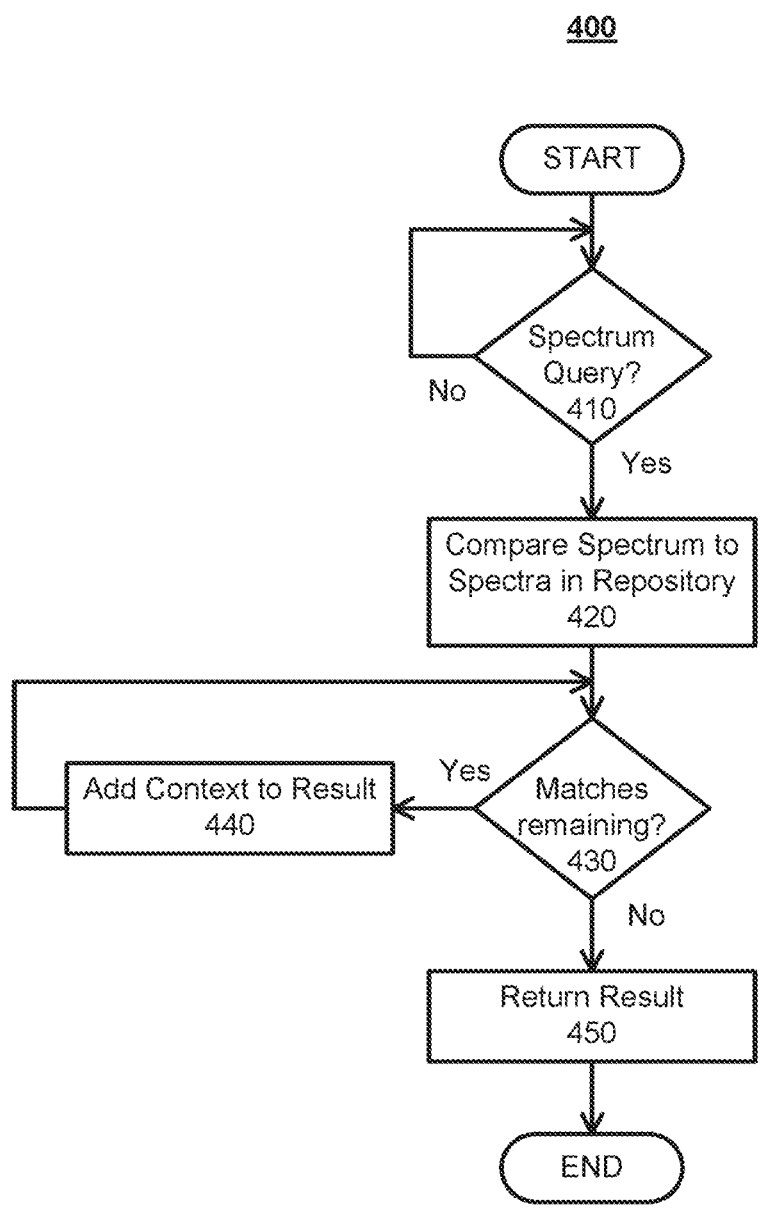
FIG. 4 is a flowchart that illustrates a process of searching a repository of a spectra, according to an embodiment.

FIG. 4 is a flowchart that illustrates a process 400 of searching repository 116, according to an embodiment. While process 400 is illustrated with a certain arrangement and ordering of steps, process 400 may be implemented with fewer, more, or different steps and a different arrangement and/or ordering of steps. Process 400 may be implemented, for example, by server application 112.

Process 400 starts in step 410, in which process 400 waits to receive a spectrum query. The spectrum query may be received in the form of a request that comprises at least a representation of a spectrum (e.g., as a vector of mass and intensity pairs, for example, representing peaks in the spectrum). In a typical implementation, the request may be submitted by a user via a client application 132 on user system 130. Client application 132 may transmit the request over network(s) 120 to server application 112 on platform 110, which receives the request in step 410. Alternatively, the spectrum query may be received from another portion of the application (e.g., another software module of server application 112 implementing step 610 of process 600 in FIG. 6). If no request is received (i.e., "No" in step 410), process 400 continues to wait to receive a spectrum query. Otherwise, whenever a request is received (i.e., "Yes" in step 410), process 400 proceeds to step 420.

As mentioned, the spectrum query may comprise a representation of a spectrum (e.g., a vector, graph, etc.). In an embodiment, MS1 isotopic profiles may be used as the spectra in the spectrum queries and repository 116. Alternatively, other types of spectra may be used.

In addition, the spectrum query may comprise additional information, including, without limitation, the precursor ion m/z value (i.e., a measure of the mass/charge for the precursor ions), and/or one or more filters to be used to restrict the search. For example, the one or more filters may comprise a window filter that restricts the search to a window of the most prominent features of the spectrum (e.g., a window of 50 Daltons that comprises the top six intensity peaks) and/or a precursor filter that removes peaks within a window around the precursor peak (e.g., by removing all intensity peaks within a 17 Dalton window around the precursor peak). Advantageously, such filters can reduce the likelihood of false positives by reducing noise.

In an embodiment, the spectrum query may also comprise additional settings or criteria to be used in the search, such as a threshold value for a similarity score (e.g., a minimum cosine score between zero and one, such as 0.7) to be used for classifying matches (described elsewhere herein as a predetermined threshold value), a minimum number (e.g., six) of peaks that must match between spectra to be classified as a match, a parent mass tolerance (e.g., 0.5), whether or not to conduct an analog search, an identification of the repositories to be searched (e.g., if more than one repository 116 is available), and/or the like.

The spectrum included in the spectrum query may comprise a spectrum (e.g., MS/MS spectrum) for any type of sample. For example, the sample could be an animal product, bodily fluids, food, personal care products, contaminants, medication formulations, pharmaceutical products, microbial species, building materials, and any other substance for which mass spectrometry (e.g., tandem mass spectrometry) can produce a mass signature.

In step 420, process 400 compares the spectrum, received in the spectrum query in step 410, to at least a subset of the spectra stored in repository 116. In a brute force implementation, process 400 could compare the received spectrum to every spectrum in every spectra sample 320 in every dataset 310 in repository 116. However, in an embodiment, process 400 may use clustering to more efficiently search the spectra in repository 116. An embodiment of one such clustering process is described elsewhere herein.

Regardless of the particular search technique used, in an embodiment, a similarity score is generated between the received spectrum and a plurality of spectra in repository 116. For example, a cosine scoring function may be used to generate the similarity scores. An embodiment of one such cosine scoring function is described elsewhere herein. Regardless of the specific scoring function used, spectra with similarity scores greater than a predetermined threshold value may be classified as matches, whereas spectra less than the predetermined threshold value may be classified as non-matches. Similarity scores equal to the predetermined threshold value may be classified as either matches or non-matches, depending on the designer's preference. The predetermined threshold value may be a system-wide setting (i.e., common to all users), a user-specific setting (e.g., specified by each user), and/or both (e.g., a system-wide default setting that can be changed by or for specific users). In an embodiment, the user may specify the predetermined threshold value to be used for a particular spectrum query. For example, the request constituting the spectrum query may also indicate the predetermined threshold value to be used for classifying matches.

In an embodiment, process 400 iterates through steps 430 and 440 for each spectrum from repository 116 that has been classified as a match in step 420 (e.g., each spectrum having a similarity score exceeding the predetermined threshold value). Specifically, if any matched spectrum remains (i.e., "Yes" in step 430), the context of that matched spectrum is added to the results in step 440. It should be understood that the application may perform these iterations serially or in parallel, depending on the particular implementation and hardware capabilities.

Step 440 may comprise adding or otherwise conveying information, representing the context of the matched spectrum, in the results. This context information may be extracted or derived from the metadata 325 associated with the spectra sample 320 comprising the matched spectrum, from the metadata 315 associated with the dataset 310 comprising the spectra sample 320 comprising the matched spectrum, and/or from metadata associated with the matched spectrum itself. Accordingly, the results will comprise a cumulative set of context information for all of the matched spectra.

In an embodiment, additional information, other than the context information, is also added to the results. Specifically, any useful (or even non-useful) information, within the metadata 325 associated with the spectra sample 320 comprising the matched spectrum, from the metadata 315 associated with the dataset 310 comprising the spectra sample 320 comprising the matched spectrum, and/or from metadata associated with the matched spectrum itself, can be added to the results. It is contemplated that this additional information could include the identity and/or structure of the molecule, even though such information is not necessary to identify the source of the molecule according to disclosed embodiments.

In an embodiment, the context information and/or additional information may be accumulated on a per-dataset basis. In other words, if a matching spectrum is within a particular dataset 310, the context and/or additional information may be derived from the metadata 325 comprising that matching spectrum's spectra sample 320. However, if two or more matching spectra are identified within the same dataset 310, the context and/or additional information may be derived from the metadata 325 associated with the spectra sample 320 comprising the matching spectrum with the highest similarity score to the spectrum received in step 410. In addition, the context and/or additional information may be derived from the metadata 315 associated with the dataset 310 comprising the matching spectrum or spectra. In its simplest form, deriving the context and/or additional information from the metadata may comprise copying the metadata into the results. In a less simple form, the context and/or additional information may be derived by extracting data from the metadata and altering that data in some manner and/or inputting that data into some other process (e.g., algorithm, function, computation, calculation, etc.) to produce the context and/or additional information. In any case, the context information and/or additional information, in the results, represent a set of consensus metadata aggregated for a particular spectrum. It should be understood that the context information in the consensus metadata may indicate one or a plurality of sources for an unknown spectrum.

In step 450, the results are returned in response to the spectrum query received in step 410. As discussed throughout, the results may comprise information related to each of the matching spectra samples 320, the accumulated metadata 325 associated with the matching spectra samples 320, and/or the accumulated metadata 315 associated with the datasets 310 comprising the matching spectra samples 320.

In a scenario in which the spectrum query was submitted by a user via client application 132, step 450 may comprise server application 112 generating a graphical user interface comprising the results (e.g., in a table, in a graph, etc.), and transmitting the graphical user interface over network(s) 120 to client application 132. Client application 132 may then render the graphical user interface on the user's user system 130. Alternatively, step 450 may comprise inputting the results into a model-generation process, which generates a model of an entire sample based on the results of a plurality of spectrum queries representing spectra for the entire sample. This model-generation process is described in more detail elsewhere herein (e.g., process 600 described with respect to FIG. 6).

Whether via the results of a single spectrum query or the results of a plurality of spectrum queries (e.g., displayed as a model of a sample), the results advantageously and efficiently provide a new set of information for research and investigation. Specifically, the context information from the results enables a researcher to identify the likely source of a sample, determine causality between samples and their sources, determine whether a particular sample is consistently related to a particular context, and/or the like. Thus, even if the structure or identity of the sample is unknown to the user and within repository 116, the context information from matching spectra can be used to derive essential information about the sample. Essentially, the context from samples in repository 116 can be transposed on a user's sample, even if the structure or identity of all of these samples remains unknown. In other words, the source of a molecule can be determined purely from a mass signature of the molecule, without first having to identify the structure of the molecule.

For example, a user may submit a spectrum query, using a spectrum obtained from performing tandem mass spectrometry on the blood sample of a patient. The application receives the spectrum query in step 410, and compares the spectrum in the spectrum query to a plurality of spectra in repository 116 in step 420. In steps 430 and 440, the application copies the context information from the metadata (e.g., metadata 315 and/or 325), associated with each match, into a data structure representing the results, which is returned in step 450. The context information in the results may indicate that the matching spectra from repository 116 have been previously seen in the context of breast cancer. Accordingly, the user may infer from the context information that the patient should be checked for breast cancer, even though the molecules in the user's blood have not been identified.

As another example, a user may submit a spectrum query, using a spectrum of an unknown molecule. The application receives the spectrum query in step 410, and compares the spectrum in the spectrum query to a plurality of spectra in repository 116 in step 420. In steps 430 and 440, the application copies the context information from the metadata (e.g., metadata 315 and/or 325), associated with each match, into a data structure representing the results, which is returned in step 450. There may be a large amount of context information in the results from a large amount of matches, and a majority of the context information may consistently indicate general microbial sources, with a certain amount of the context information indicating a *Streptomyces* species. Accordingly, the user may infer from the consistency of the context information that the unknown molecule is microbial in origin, and likely of the *Streptomyces* species (e.g., Stenothricin).

2.2. Example of Cluster-Based Search

As discussed above, step 420 could comprise a brute-force search in which the spectrum in the spectrum query is compared to every spectrum in repository 116. However, such a technique is not scalable for very large repositories. Accordingly, in an embodiment, step 420 comprises a cluster-based search, which can improve the speed of each search by orders of magnitude. For example, in one test, searching for a spectrum across a very large repository 116 without clustering took eight hours, whereas searching for the spectrum using clustering took only ten minutes. While clustering may result in the loss of some matches which would occur in a brute-force search, this loss of sensitivity is generally only noticeable with very rare molecules. One example of a cluster-based search is described in "Clustering Millions of Tandem Mass Spectra," by Frank et al., Journal of Proteome Research 2008, 7, pp. 113-122, which is hereby incorporated herein by reference as if set forth in full.

Clustering may be performed across the spectra in all of the datasets 310 in repository 116, or may be performed separately for each dataset 310 (i.e., for the spectra within each dataset 310). In either case, whether repository-wide or dataset-wide, similar spectra are grouped together into a cluster (e.g., using normalized dot-products of the spectra). For example, in a bottom-up approach, each spectra may be initially assigned to its own single-spectrum cluster. Then, clusters with similar spectra are merged into larger clusters. Specifically, a similarity score may be computed for two clusters, and, when the similarity score exceeds a predetermined threshold value, all of the spectra in the two clusters may be merged into a single cluster. The similarity score and predetermined threshold value may be selected according to the design goals of a particular implementation. It should be understood that a higher threshold value will result in a larger number of overall clusters and a lower threshold value will result in a fewer number of overall clusters. To increase the number of matches found in step 420, a relatively low threshold value should be used. However, this may also result in an increase in the number of spurious matches.

For each cluster, a single representative spectrum is determined for that cluster. The single representative spectrum for a given cluster may be an actual spectrum within the cluster (e.g., the spectrum with the highest signal-to-noise ratio) or a virtual spectrum (e.g., a consensus spectrum constructed by consolidating the peaks of all spectra in the cluster). For any single-spectrum clusters, the representative spectrum would generally be the lone spectrum within the cluster. However, in an embodiment, clusters with less than a predetermined number of spectra (e.g., less than two spectra) are discarded. Generally, single-spectrum clusters should be discarded, because a spectrum that is not seen more than once is likely noise, since noise typically does not cluster with other noise.

In contrast to a brute-force search, the spectrum in the spectrum query does not need to be compared to every spectra in repository 116. Rather, using a cluster-based search, the spectrum in the spectrum query only needs to be compared against the single representative spectrum for each cluster. Accordingly, it is preferable to use a cluster-based search in step 420 over a brute-force search. However, it should be understood that other types of searches may be used in step 420, other than a cluster-based search or a brute-force search, and that such searches may represent an improvement in efficiency over a cluster-based search and/or brute-force search. In any case, the particular search technique chosen should appropriately balance the competing goals of match accuracy and search speed.

In an embodiment, the spectra in each cluster retain their associations to their respective spectra sample 320 and/or dataset 310. For example, a mapping may be stored that maps the spectra in each cluster to the original spectra in their respective datasets 310. Thus, once a cluster is identified, the metadata 325 and/or 315 for one or more, and potentially all, of the spectra within the cluster may be retrieved. In this manner, metadata may be accumulated during the search.

Figure 5:
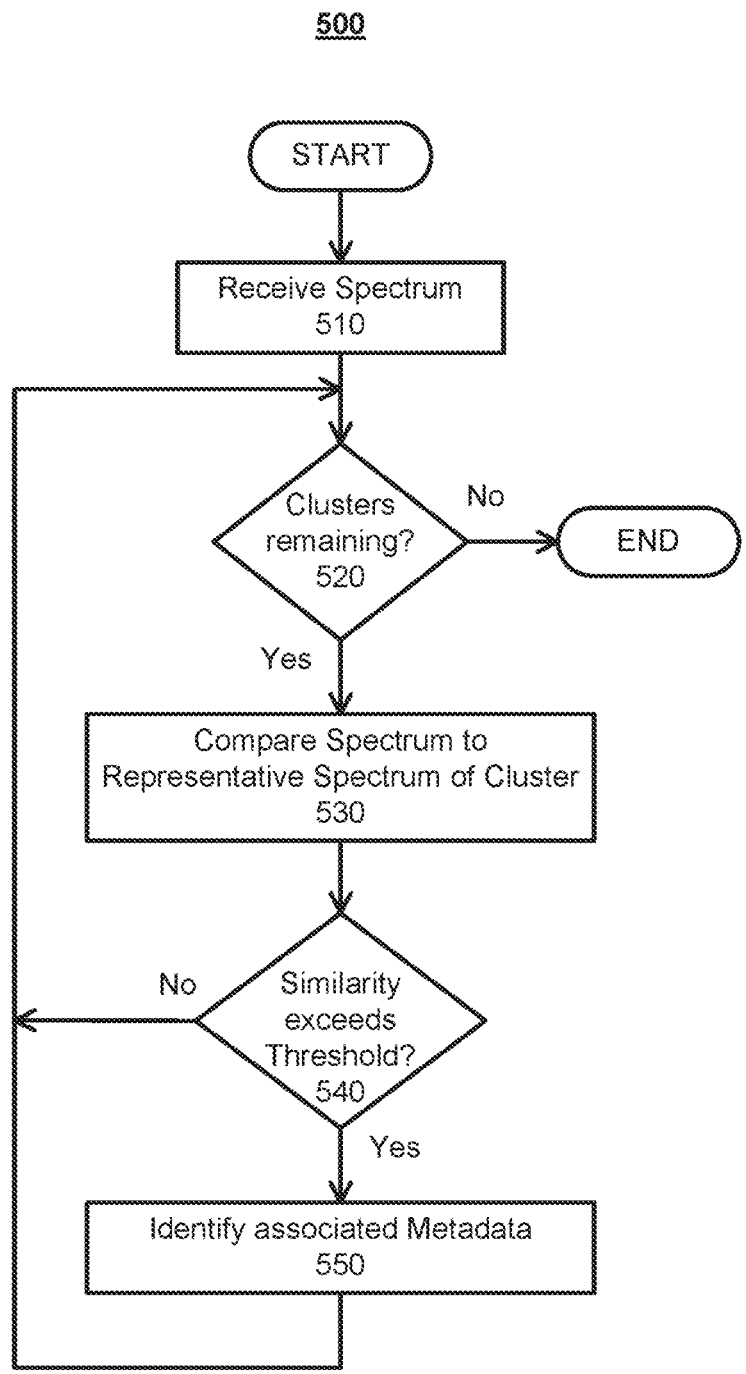
FIG. 5 is a flowchart that illustrates a cluster-based search process, according to an embodiment.

FIG. 5 is a flowchart that illustrates a cluster-based search process 500, according to an embodiment. Process 500 may correspond to steps 420-440 in process 400. While process 500 is illustrated with a certain arrangement and ordering of steps, process 500 may be implemented with fewer, more, or different steps and a different arrangement and/or ordering of steps. Process 500 may be implemented by server application 112.

Process 500 starts in step 510, in which process 500 receives a spectrum (e.g., from a spectrum query). Then, process 500 iterates through steps 520-540 and potentially step 550 (when a match is found) for each cluster of spectra to be searched. It should be understood that server application 112 may perform these iterations serially or in parallel, depending on the particular implementation and hardware capabilities.

In step 520, process 500 determines whether or not any clusters remain to be compared to the spectrum received in step 510. If any clusters remain (i.e., "Yes" in step 520), process 500 proceeds to step 530. Otherwise, if no cluster remains (i.e., "No" in step 520), process 500 ends.

In step 530, the spectrum, received in step 510, is compared to the representative spectrum of the next cluster to be considered. In an embodiment, step 530 may utilize a cosine scoring function to generate a similarity score, as described elsewhere herein. For example, a cosine scoring function may comprise a dot-product function that measures the cosine of the angle between vectors representing the spectra being compared. The method of scoring used in step 530 may be the same as or different than the method of scoring used to generate the clusters, as described elsewhere herein. Alternatively, another scoring technique may be used to measure the similarity between the two spectra. Other scoring techniques include, without limitation, Euclidean distance (e.g., sum of the squares of the differences between chosen weighted peak intensities), absolute value distances (e.g., sum of the absolute differences between chosen weighted peak intensities), probability-based matching (e.g., using peak occurrence statistics), Hertz similarity index, shared peak count, Manhattan distance, Jaccard distance, and the like. In an embodiment, a similarity score can be generated by combining two or more scoring functions (e.g., a cosine scoring function in combination with a shared peak count). Scoring functions can be combined in any well-known manner (e.g., average, weighted average, etc.).

In step 540, process 500 compares the similarity score generated in step 530 to a predetermined threshold value. As discussed elsewhere herein, the predetermined threshold value may be a system-wide and/or user-specified setting. The predetermined threshold value used in step 540 may be the same as or different (e.g., higher) than the predetermined threshold value used to generate clusters. If the similarity score is greater than, and optionally equal to, the predetermined threshold value (i.e., "Yes" in step 540), the current cluster is classified as a match, and process 500 proceeds to step 550. Otherwise, if the similarity score is less than the predetermined threshold value (i.e., "No" in step 540), the current cluster is not classified as a match, and process 500 returns to step 520 to compare the spectrum to another cluster, if any.

In step 550, process 500 may identify (e.g., retrieve) metadata associated with the matching cluster. The metadata may be metadata aggregated from the metadata 315 and/or 325 for all or a subset of the spectra in the matching cluster. Alternatively, process 500 could compare the spectrum, received in step 510, to each of the spectrum in the matching cluster, for example, using the same computation for similarity scores, but a higher predetermined threshold value for determining each individual matching spectrum in the matching cluster. Process 500 could then identify the metadata 325 associated with the spectra sample 320 comprising the matched spectrum, the metadata 315 associated with the dataset 310 comprising the spectra sample 320 comprising the matched spectrum, and/or the metadata associated with the matched spectrum itself. In any case, the identified metadata may comprise context information. Accordingly, once process 500 is complete, circumstantial context information has been identified and, in an embodiment, retrieved for the spectrum received in step 510.

2.3. Example of Cosine Scoring

As discussed above, step 530 may comprise generating a similarity score between two spectra. While any of a variety of methods may be used to generate the similarity score, in an embodiment, cosine scoring is used. One example of a cosine scoring function is described in "Optimization and Testing of Mass Spectral Library Search Algorithms for Compound Identification," by Stein et al., J. Am. Soc. Mass. Spectrum 1994, 5, pp. 859-866, which is hereby incorporated herein by reference as if set forth in full.

In an embodiment, the similarity score represents a probability or likelihood (e.g., from a value of zero, representing a definite non-match, to a value of one, representing a definite match) that the two spectra, being compared, represent the same molecule. This is vital, since the spectra for the same molecule may differ, for example, due to differences in instrumentation and analysis conditions.

In an embodiment, each spectrum, received from a user and/or stored in repository 116, may be represented as a vector. Alternatively, the application may convert the spectra into vectors when comparing them. In either case, each vector representation of a spectrum may comprise a row vector comprising the ordered peak intensities in the mass spectrum. Regardless of when or how the vectors are generated, in an embodiment, the similarity score is generated by computing the cosine of the angle (dot product) between the vector representations of the spectra being compared. In addition, performance of the cosine scoring function may be optimized by varying the scaling (e.g., compressing the range of mass spectral peak intensities) and mass weighting (e.g., placing an increased weighting on higher mass peaks) of the peak intensities in each spectrum. The optimized cosine scoring function may be further enhanced by measuring relative intensities between corresponding peaks in two spectra, and increasing the importance of this measure, within the dot product, as the proportion of common peaks increases.

2.4. Modeling a Sample

In an embodiment, an entire sample, represented as a plurality of spectra, may be searched against repository 116. In other words, processes 400 and/or 500 may be executed (e.g., by server application 112) over a plurality of iterations, with each of the plurality of spectra, from the sample, being provided in separate spectrum queries or in one aggregate spectrum query. A model of the constituent molecules in the sample may then be generated (e.g., by server application 112) from the results and provided to a user (e.g., in a graphical user interface). In other words, an entire sample may be decomposed into its constituent sources (represented in the context information of the results), which may be modeled as a molecular network.

Figure 6:
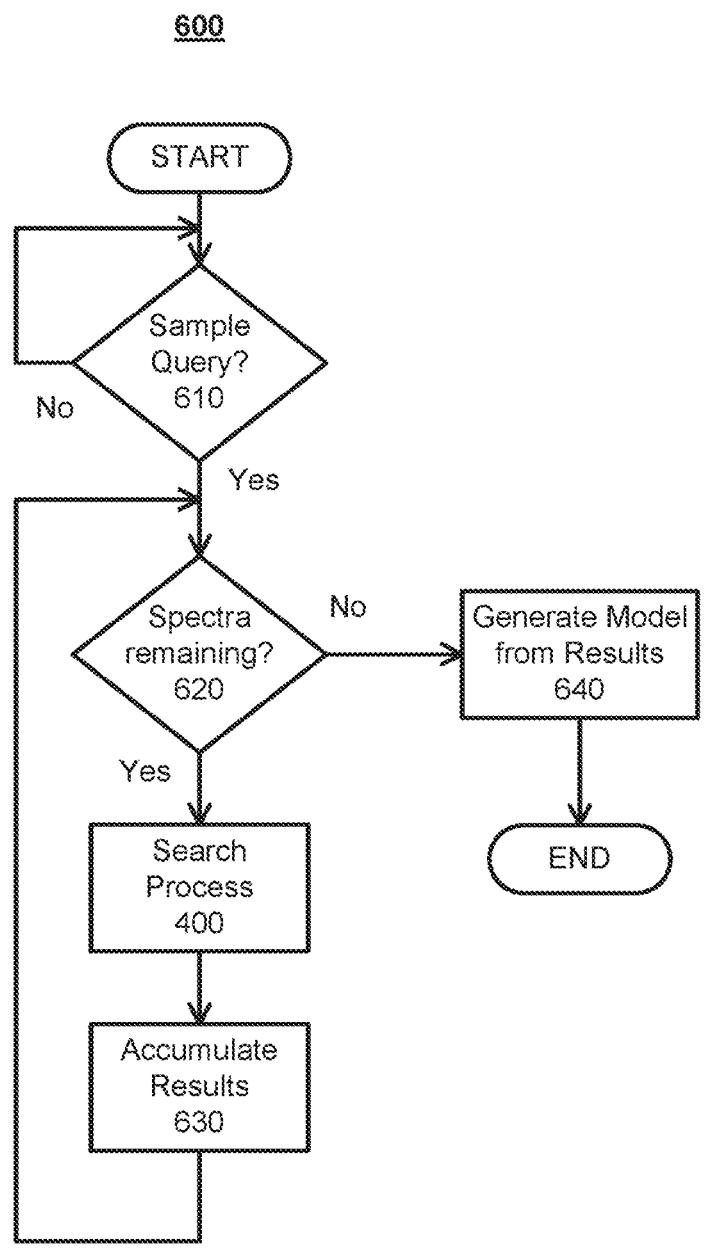
FIG. 6 is a flowchart that illustrates a process for generating a model of an entire sample, according to an embodiment.

FIG. 6 is a flowchart that illustrates a process 600 for generating a model of an entire sample, according to an embodiment. While process 600 is illustrated with a certain arrangement and ordering of steps, process 600 may be implemented with fewer, more, or different steps and a different arrangement and/or ordering of steps. Process 600 may be implemented by server application 112.

Process 600 starts in step 610, in which process 600 waits to receive a sample query. The sample query may be received in the form of a request that comprises at least a representation of a sample (e.g., as a plurality of spectra vectors). In a typical implementation, the request may be submitted by a user via a client application 132 on user system 130. Client application 132 may transmit the request over network(s) 120 to server application 112 on platform 110, which receives the request in step 610. If no request is received (i.e., "No" in step 610), process 600 continues to wait to receive a sample query. Otherwise, whenever a request is received (i.e., "Yes" in step 610), process 600 proceeds to step 620.

As mentioned, the representation of the sample in the sample query may comprise a plurality of representations (e.g., vectors, graphs, etc.) for a plurality of spectra in the sample. A typical biological sample may comprise thousands of spectra corresponding to thousands of molecules. In addition to representations of spectra, the sample query may comprise additional sample-wide information and/or spectra-specific information. For example, the sample query may comprise the same information (e.g., precursor ion m/z value, one or more filters, predetermined threshold value for the similarity score, minimum number of matching peaks, parent mass tolerance, analog search indication, identification of repositories to be searched, etc.) as the spectrum query, discussed elsewhere herein, for each individual spectrum in the sample and/or for the sample as a whole.

In an embodiment, process 600 iterates through steps 620, 400, and potentially 630 (when a match is found), for each individual spectrum represented in the sample query. In step 620, process 600 determines whether or not any spectra, from the sample query received in step 610, remain to be considered. If any spectra remain (i.e., "Yes" in step 620), process 600 proceeds to process 400. Otherwise, if no spectra remain (i.e., "No" in step 620), process 600 proceeds to step 640.

In process 400, the next spectrum from the sample query is searched against repository 116 (e.g., using cluster-based search process 500). Process 400 is described above with respect to FIG. 4. The results of process 400 (i.e., representing matches from repository 116), which may comprise context information and optionally additional information for each matched spectrum, are accumulated in step 630. The context information and/or additional information in the accumulated results represent a set of consensus metadata aggregated for a particular sample.

The context information in the consensus metadata may indicate one or a plurality of sources for a single unknown sample. For example, the consensus metadata may indicate that the sample was derived from a mixture of sources (e.g., multiple brands of personal care products in addition to a pharmaceutical agent). As discussed elsewhere herein, an inference can be made that the source(s) identified in the search for a sample are the source(s) of the sample. The inference is stronger when the same source(s) appear consistently within the consensus metadata (e.g., the results comprise a plurality of similar or identical context information derived from metadata associated with a plurality of discrete matching spectra and/or their respective datasets in repository 116). Conversely, the inference is weaker for sources which appear sporadically or inconsistently within the consensus metadata. In other words, the more a particular context appears in the results, the stronger the inference is that the spectrum or sample originated in that context, and the less a particular context appears in the results, the weaker the inference is that the spectrum or sample originated in that context. Thus, in an embodiment, a consistency score can be generated that represents the strength of each inference for each context represented in the context information of the results. The consistency score may be generated, for each context in the context information of the consensus metadata, based on how frequently or consistently that context appears in the context information (e.g., relative to other contexts that are present in the context information).

In step 640, process 600 generates a model of the sample, represented in the sample query, based, at least in part, on the results, accumulated in step 630, for all of the spectra represented in the sample query. The model may be returned in response to the sample query received in step 610. In a scenario in which the sample query was submitted by a user via client application 132, step 640 may comprise the server application 112 generating the model, and transmitting the model (e.g., within a graphical user interface, or as a discrete data object) over network(s) 120 to client application 132. Client application 132 may then render the model on the user's user system 130.

As an example, a user may submit a sample query representing a stool sample from a patient. Process 600 searches for each spectrum in the sample query to generate accumulated results comprising context information for each of spectrum in the sample query. The context information may represent the source of each molecule represented in the spectra of the stool sample. In the case of the stool sample, at least a subset of the sources will represent the foods eaten by the patient. For example, the context information for one or a plurality of the molecules (represented as spectra) may indicate that these molecules have been previously seen in apples, the context information for another one or a plurality of molecules (represented as other spectra) may indicate that these other molecule(s) have been previously seen in tuna fish, and so on and so forth. Previous meal(s) of the patient can then be inferred from this context information. For example, from these results, one could infer that the patient has recently consumed apples and fish, or some product thereof.

In an embodiment, for any given molecule represented in a sample query or spectrum query, the application may identify one or more approximate molecules and match each spectrum for those approximate molecule(s) to reference spectra in repository 116 (e.g., according to process 400) to retrieve context information for those approximate molecule(s). In other words, the application may retrieve context information for reference molecule(s) in repository 116 that match the molecule(s) in the query, as well as context information for reference molecule(s) in repository 116 that match approximate molecule(s) to the molecule(s) in the query.

Figure 7:
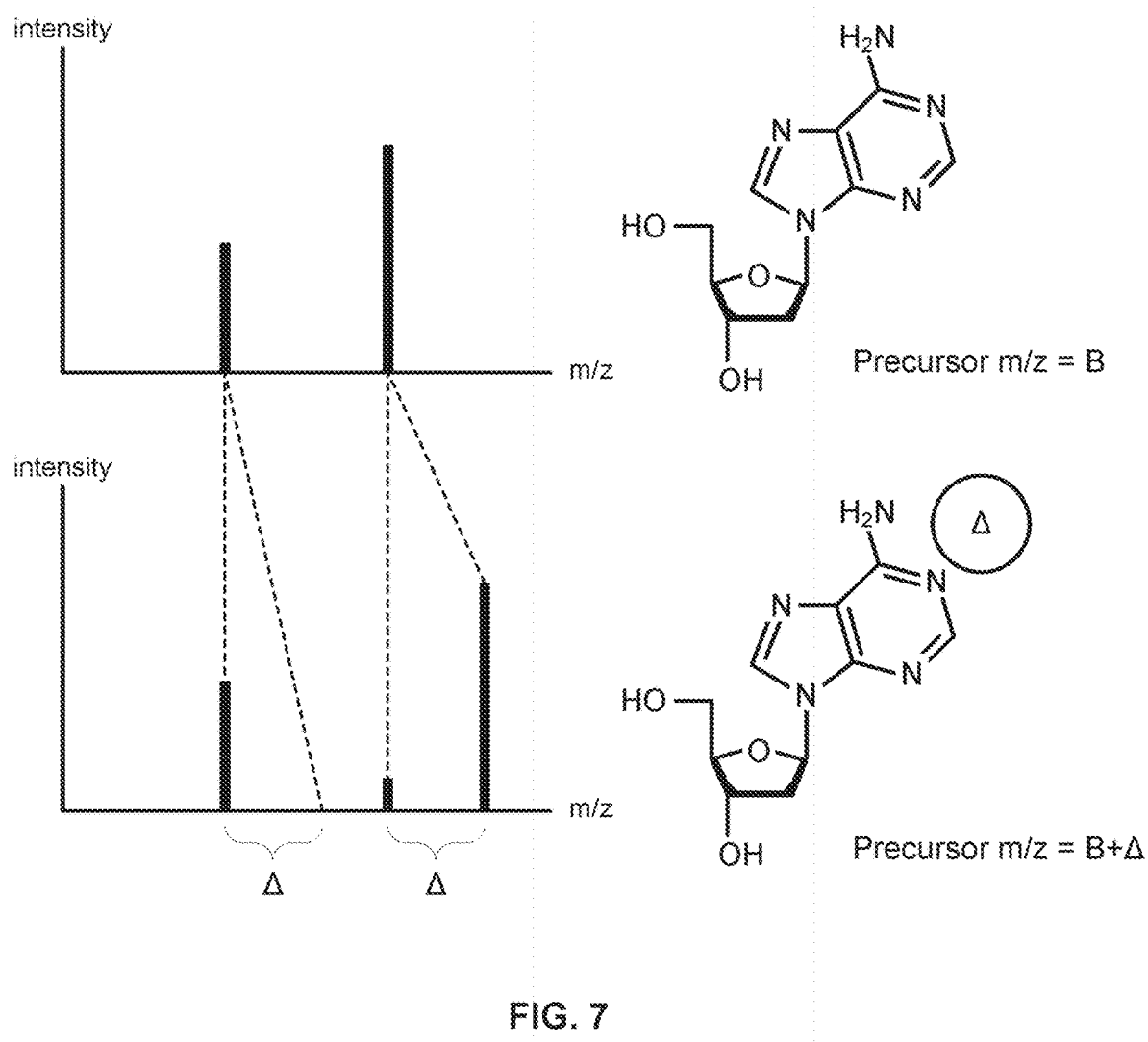
FIG. 7 illustrates how two molecules are determined to be approximate to each other, according to an embodiment.

FIG. 7 illustrates how two molecules are determined to be approximate, according to an embodiment. Specifically, the molecule from a query is represented by the upper example spectrum, whereas an approximate molecule is represented by the lower example spectrum. The two molecules differ by a delta in mass (i.e., m/z), which may represent a single structural difference at a single location. The molecule and the approximate molecule may represent the same molecule but with one of the molecules having been altered. An example process for determining approximate molecules is disclosed by the variable dereplication process described in "Sharing and community curation of mass spectrometry data with Global Natural Products Social Molecular Networking," by Wang et al., Natural Biotechnology 34, pp. 828-37 (2016), which is hereby incorporated herein by reference as if set forth in full. Specifically, the matching of peaks between two spectra is formulated as a maximum bipartite matching problem, in which peaks from query spectra and reference spectra in repository 116 are represented as nodes, with edges connecting the peaks in a query spectrum to those peaks in a reference spectrum that are within a system-defined or user-defined fragment mass tolerance (i.e., the delta). The bipartite match of peaks that maximizes the normalized dot product of the two spectra is selected, and the highest scoring reference spectrum or spectra for each query spectrum is identified as an approximate molecule. An additional example process for determining approximate molecules is disclosed in "Mass spectral molecular networking of living microbial colonies," by Watrous et al., Proceedings of the National Academy of Sciences (PNAS), May 14, 2012, E1743-52, which is also hereby incorporated herein by reference as if set forth in full. As mentioned above, the spectra for both the molecule and any approximate molecules (i.e., whose spectra match except for the delta) may be compared against reference spectra in repository 116, and context information may be retrieved for both the molecule and any approximate molecules, for example, utilizing process 400 for both the molecule and any approximate molecules.

In an embodiment, all of datasets 310 in repository 116 may be represented in a single graphical network to visualize the relationships between datasets 310. For example, if a spectrum in a query matches to a reference spectrum, representing a molecule and represented as a node in the network, that node may be rendered in a navigable network within a graphical user interface of the application. A user may navigate between the node and neighboring nodes to explore the context information for connected molecules within the network. In this manner, a user may develop an understanding of all of the different contexts in which the same, similar, or approximate molecules appear.

3. Examples

Disclosed embodiments may be used in a variety of different settings. For example, in the agricultural industry, the disclosed embodiments can be used to identify the sources of contamination in a water sample, soil sample, food sample, and/or the like. For drug discovery, the disclosed embodiments can be used to find high productivity sources of scarce, but highly desirable, molecules. In the medical setting, the disclosed embodiments can be used to identify the source of a harmful molecule or irritant, in order to improve health. In medicine, the disclosed embodiments can be used to objectively determine a subject's diet or food consumption, monitor a patient's compliance with prescribed medication, and/or determine a subject's compliance in a clinical trial. In the biosecurity industry, the disclosed embodiments can be used to identify the source of unknown and potentially toxic and/or dangerous substances. In the setting of proteomics, disclosed embodiments can advantageously be used to analyze small molecules, rather than proteins and peptides, without specifically relying on identifying the small molecules.

Figure 8:
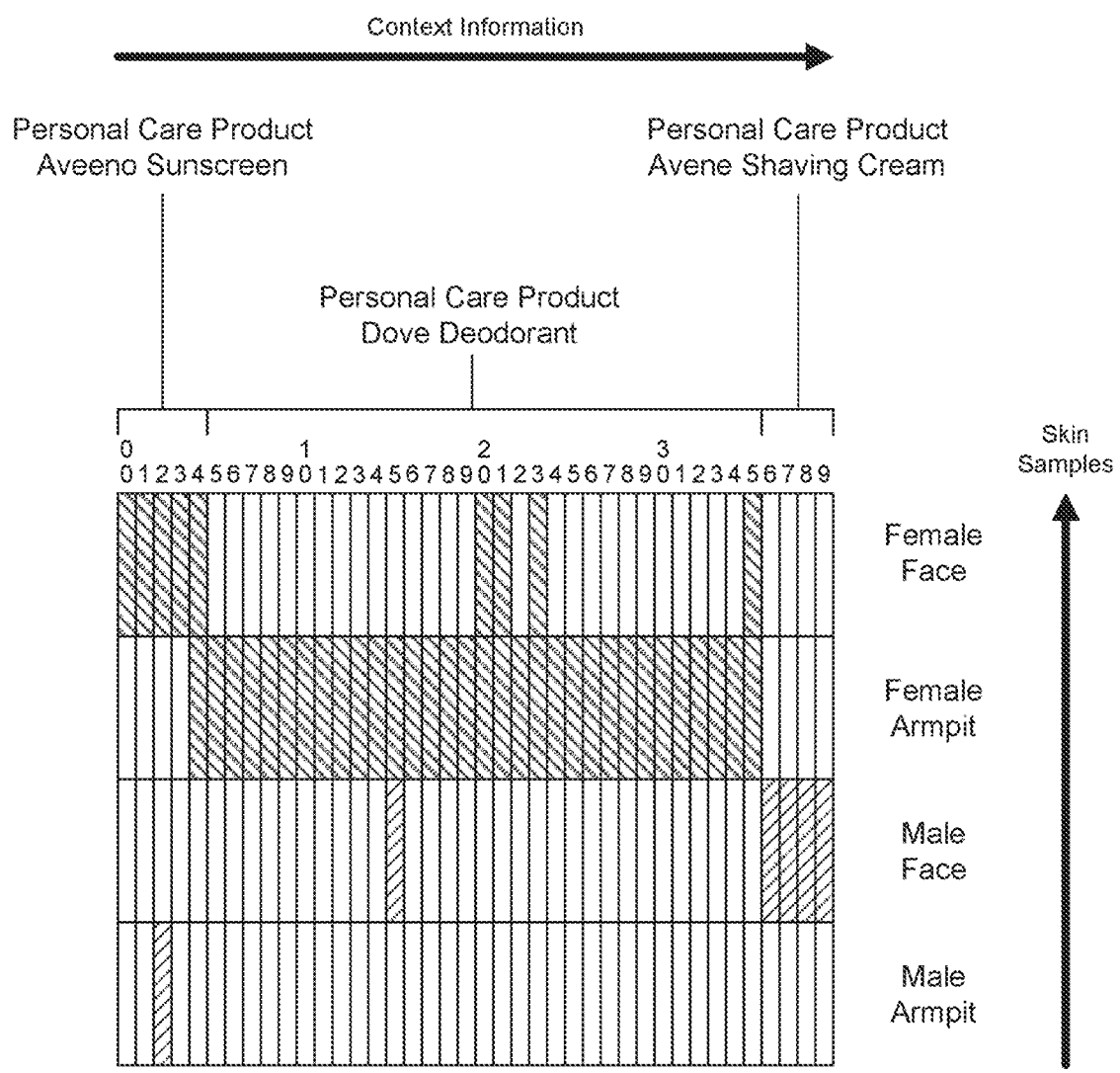
FIG. 8 illustrates how inferences can be made about samples based on context information returned by disclosed embodiments, according to several examples.

FIG. 8 illustrates how inferences can be made about samples based on context information returned by disclosed embodiments, according to several examples. In the illustrated examples, repository 116 includes a plurality of spectra 00-39 which are each associated with context information indicating that the spectra were previously seen in molecules from a "personal care product." In addition, each of spectra 00-04 are associated with context information indicating that their source was "Aveeno sunscreen," each of spectra 05-35 are associated with context information indicating that their source was "Dove Deodorant," and each of spectra 36-39 are associated with context information indicating that their source was "Avene shaving cream." Four skin samples were submitted from a male armpit, male face, female armpit, and female face, for example, using a sample query or spectrum query as described elsewhere herein. These skin samples were searched against repository 116 to generate the results illustrated in FIG. 8. Specifically, FIG. 8 illustrates that at least one spectrum from the skin sample from the male armpit matched reference spectrum 03, that spectra from the skin sample from the male face matched reference spectra 15 and 36-39, that the spectra from the skin sample from the female armpit matched reference spectra 04-35, and that spectra from the skin sample from the female face matched reference spectra 00-04, 20, 21, 23, and 35.

Based on the fact that spectra from the skin sample from the male armpit matched spectrum 03, an inference may be made that the male is using a personal care product, and more particularly Aveeno sunscreen, on his armpit. However, given that only one spectrum was matched, this inference is relatively weak.

Based on the fact that spectra from the skin sample from the male face matched spectra 36-39, a first inference may be made that the male is using a personal care product, and more particularly Avene shaving cream, on his face. Given that a significant number of multiple spectra were matched, this first inference is relatively strong. In addition, based on the fact that spectra from the skin sample from the male face matched spectrum 15, a second inference may be made that the male is using a personal care product, and more particularly Dove deodorant, on his face. However, given that only one spectrum was matched, this inference concerning Dove deodorant is relatively weak, while the inference concerning the use of a personal care product in general remains relatively strong due to the first inference.

Based on the fact that spectra from the skin sample from the female armpit matched spectra 05-35, a first inference may be made that the female is using a personal care product, and more particularly Dove deodorant, on her armpit. Given that a large number of multiple spectra were matched, this first inference is relatively strong. In addition, based on the fact that spectra from the skin sample from the female armpit matched spectrum 04, a second inference may be made that the female is using a personal care product, and more particularly Aveeno sunscreen, on her armpit. However, given that only one spectrum was matched, this inference concerning Aveeno sunscreen is relatively weak, while the inference concerning the use of a personal care product in general remains relatively strong due to the first inference.

Based on the fact that spectra from the skin sample from the female face matched spectra 00-04, a first inference may be made that the female is using a personal care product, and more particularly, Aveeno sunscreen, on her face. Given that a significant number of multiple spectra were matched, this first inference is relatively strong. In addition, based on the fact that the skin sample from the female face matched spectra 20, 21, 23, and 35, a second inference may be made that the female is using a personal care product, and more particularly Dove deodorant, on her face. However, given that only a small fraction of spectra were matched, this inference concerning Dove deodorant is relatively weak, while the inference concerning the use of a personal care product in general remains relatively strong due to the first inference. Assuming that the female skin samples were acquired from the same female, the fact that the skin samples from both the armpit and face matched spectra for Aveeno sunscreen and Dove deodorant raises a relatively strong inference that the female uses both Aveeno sunscreen and Dove deodorant as personal care products.

The above description of the disclosed embodiments is provided to enable any person skilled in the art to make or use the invention. Various modifications to these embodiments will be readily apparent to those skilled in the art, and the general principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

Combinations, described herein, such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, and any such combination may contain one or more members of its constituents A, B, and/or C. For example, a combination of A and B may comprise one A and multiple B's, multiple A's and one B, or multiple A's and multiple B's.

What is claimed is:

1. A method comprising:
   determining, by at least one hardware processor, a plurality of clusters of reference mass spectra stored in one or more databases, individual clusters of the plurality of clusters including a number of reference mass spectra having at least a threshold amount of similarity, wherein the plurality of clusters are determined by:
      determining, by the at least one hardware processor, an initial cluster for individual reference mass spectra of the number of reference mass spectra to determine a plurality of initial clusters, wherein the individual reference mass spectra are represented by a vector that indicates ordered peak intensities of the individual reference mass spectra,
      determining, by the at least one hardware processor, a similarity score between pairs of the plurality of initial clusters by analyzing features of vectors of the pairs of the plurality of initial clusters, and
      merging, by the at least one hardware processor, one or more of the initial clusters into a single cluster in response to the similarity score being at least a threshold similarity score;
   determining, by the at least one hardware processor and for the individual clusters of the plurality of clusters, a representative spectrum;
   obtaining a biological sample from a patient, wherein the biological sample includes a plurality of molecules;
   performing tandem mass spectrometry with respect to the biological sample to generate a plurality of query mass spectra, individual query mass spectra of the plurality of mass spectra, corresponding to one or more molecules of the plurality of molecules;
   receiving, by the at least one hardware processor, a spectrum query comprising a representation of a query mass spectrum of the plurality of query mass spectra, the query mass spectrum corresponding to a molecule of the plurality of molecules;
   searching, by the at least one hardware processor, the one or more databases for the query mass spectrum by, for individual representations of a first plurality of representations of reference mass spectra in the one or more databases:
      generating, by the at least one hardware processor an additional similarity score between the representation of the query mass spectrum and the individual representations of the reference mass spectrum, wherein the individual representations of the reference mass spectrum corresponds to the representative spectrum of an individual cluster of the plurality of clusters,
      responsive to determining that the additional similarity score exceeds a predetermined threshold value, and without utilizing a molecular identity of a molecule represented by the reference mass spectrum, retrieving, by the at least one hardware processor, metadata associated with the reference mass spectrum,
      deriving, by the at least one hardware processor, context information from the retrieved metadata, and
      adding, by the at least one hardware processor, the context information to consensus metadata associated with the query mass spectrum, wherein the context information indicates a source of the reference mass spectrum; and
   generating, by the at least one hardware processor, user interface data that corresponds to a user interface that includes a navigable molecular network, the molecular network include a plurality of connected nodes with individual nodes of the plurality of connected nodes corresponding to at least one molecule in the biological sample that is matched with one or more reference spectra, and wherein the individual nodes are selectable to display at least a portion of context information for the at least one molecule of the individual node.

2. The method of claim 1, further comprising using the at least one hardware processor to:
   analyze the number of reference mass spectra having at least a threshold amount of similarity, for an individual cluster of the plurality of clusters to determine a consensus reference spectrum by consolidating peaks of the number of reference mass spectra included in the individual cluster, wherein the representative spectrum of the individual cluster includes the consensus reference spectrum.

3. The method of claim 1, wherein generating the additional similarity score between the representation of the query mass spectrum and the individual representation of the reference mass spectrum comprises computing a cosine of an angle between a first vector representation of the query mass spectrum and a second vector representation of the individual reference mass spectrum.

4. The method of claim 3, wherein generating the additional similarity score between the representation of the query mass spectrum and the individual representations of the reference mass spectrum further comprises computing a shared peak count between the query mass spectrum and the reference mass spectrum.

5. The method of claim 1, further comprising performing a plurality of iterations of searching the one or more databases for the query mass spectrum in relation to the individual representations of the first plurality of representations of the reference mass spectra in the one or more databases, wherein at least a portion of the plurality of iterations are performed in parallel by a computational platform.

6. The method of claim 1, wherein the first plurality of representations of reference mass spectra used in the search are at least a subset of a second plurality of representations of reference mass spectra in the one or more databases, wherein the method further comprises using the at least one hardware processor to store the second plurality of representations of reference mass spectra in the one or more databases in a plurality of datasets, and wherein each dataset represents a single context, such that each of the representations of reference mass spectra within each dataset represents a molecule obtained within the single context of that dataset.

7. The method of claim 6, wherein each of the plurality of datasets comprises a plurality of spectra samples, wherein each of the plurality of spectra samples in each dataset comprises one or more of the second plurality of representations of reference mass spectra that represent a molecule obtained from a single sample within the single context of that dataset.

8. The method of claim 7, wherein each of the plurality of spectra samples in each of the plurality of datasets is associated with sample-specific metadata, and wherein the retrieved metadata associated with a reference mass spectrum comprises the sample-specific metadata associated with the spectra sample that comprises a representation of the reference mass spectrum.

9. The method of claim 6, wherein, when the additional similarity scores between the representation of the query mass spectrum and two or more of the first plurality of individual representations of reference mass spectra within a same dataset all exceed the predetermined threshold value, only the context information, from the metadata associated with one of the two or more individual representations of reference mass spectra having a highest similarity score, is added to the consensus metadata.

10. The method of claim 6, wherein each of the plurality of datasets is associated with dataset-specific metadata, and wherein the retrieved metadata associated with a reference mass spectrum comprises dataset-specific metadata associated with the dataset that comprises a representation of the reference mass spectrum.

11. The method of claim 4, wherein the context information in the consensus metadata indicates a plurality of distinct sources and wherein the first plurality of representations of the reference mass spectrum correspond to thousands of spectra.

12. The method of claim 1, wherein the spectrum query comprises one or more filters, and wherein the search is restricted in accordance with the one or more filters.

13. The method of claim 12, wherein the one or more filters comprise a window filter that restricts the search to a window that represents only a portion of the query mass spectrum.

14. The method of claim 12, wherein the one or more filters comprise a precursor filter that removes peaks around a precursor peak within a window that represents only a portion of the query mass spectrum.

15. The method of claim 1, further comprising using the at least one hardware processor to, for each of the first plurality of representations of reference mass spectra in the one or more databases, when the additional similarity score exceeds the predetermined threshold value and when the retrieved metadata associated with the reference spectrum comprises the molecular identity of the molecule represented by the reference mass spectrum, add the molecular identity of the molecule represented by the reference mass spectrum to the consensus metadata associated with the query mass spectrum.

16. The method of claim 1, further comprising using the at least one hardware processor to:
receive a sample query comprising a representation of a sample, wherein the representation of the sample comprises a plurality of representations of query mass spectra of molecules within the sample; and
generate a spectrum query and search the one or more databases for each of the plurality of query mass spectra to generate consensus metadata that includes context information for all of the query mass spectra.

17. The method of claim 1, further comprising using the at least one hardware processor to:
identify at least one approximate mass spectrum that differs by a mass tolerance from the query mass spectrum; and search the one or more databases for the at least one approximate mass spectrum by, for each of the first plurality of representations of reference mass spectra in the one or more databases,
generating a similarity score between a representation of the approximate mass spectrum and the representation of the reference mass spectrum,
when the similarity score exceeds a predetermined threshold value, without utilizing a molecular identity of a molecule represented by the reference mass spectrum, retrieving metadata associated with the reference mass spectrum, and derive context information from the retrieved metadata, and
adding the context information to the consensus metadata, wherein the context information indicates a source of the reference mass spectrum.

18. The method of claim 1, wherein at least a portion of the plurality of molecules of the biological sample are not included in reference mass spectra of the one or more databases.

19. A system comprising:
at least one hardware processor; and
one or more software modules that, when executed by the at least one hardware processor:
determine a plurality of clusters of reference mass spectra stored in one or more databases, individual clusters of the plurality of clusters including a number of reference mass spectra having at least a threshold amount of similarity, wherein the plurality of clusters are determined by:
determining an initial cluster for individual reference mass spectra of the number of reference mass spectra to determine a plurality of initial clusters, wherein the individual reference mass spectra are represented by a vector that indicates ordered peak intensities of the individual reference mass spectra,
determining a similarity score between pairs of the plurality of initial clusters by analyzing features of vectors of the pairs of the plurality of initial clusters, and
merging one or more of the initial clusters into a single cluster in response to the similarity score being at least a threshold similarity score;
determine, for the individual clusters of the plurality of clusters, a representative spectrum;
receive a spectrum query comprising a representation of a query mass spectrum of a molecule,
search the one or more databases for the query mass spectrum by, for individual representations of a first plurality of representations of reference mass spectra in the one or more databases:
generating an additional similarity score between the representation of the query mass spectrum and the individual representation of the reference mass spectrum, wherein the individual representation of the reference mass spectrum corresponds to the representative spectrum of an individual cluster of the plurality of clusters,
responsive to determining that the additional similarity score exceeds a predetermined threshold value, and without utilizing a molecular identity of a molecule represented by the reference mass spectrum, retrieving metadata associated with the reference mass spectrum,
deriving context information from the retrieved metadata, and adding the context information to consensus metadata associated with the query mass spectrum, wherein the context information indicates a source of the reference mass spectrum, and generating user interface data that corresponds to a user interface that includes a navigable molecular network, the molecular network include a plurality of connected nodes with individual nodes of the plurality of connected nodes corresponding to at least one molecule that is matched with one or more reference spectra, and wherein the individual nodes are selectable to display at least a portion of context information for the at least one molecule of the individual node.

20. A non-transitory computer-readable medium having instructions stored therein, wherein the instructions, when executed by a processor, cause the processor to:

determine a plurality of clusters of reference mass spectra stored in one or more databases, individual clusters of the plurality of clusters including a number of reference mass spectra having at least a threshold amount of similarity, wherein the plurality of clusters are determined by:

determining an initial cluster for individual reference mass spectra of the number of reference mass spectra to determine a plurality of initial clusters, wherein the individual reference mass spectra are represented by a vector that indicates ordered peak intensities of the individual reference mass spectra, determining a similarity score between pairs of the plurality of initial clusters by analyzing features of vectors of the pairs of the plurality of initial clusters, and merging one or more of the initial clusters into a single cluster in response to the similarity score being at least a threshold similarity score;

determine, for the individual clusters of the plurality of clusters, a representative spectrum;

receive a spectrum query comprising a representation of a query mass spectrum of a molecule;

search the one or more databases for the query mass spectrum by, for individual representations of a first plurality of representations of reference mass spectra in the one or more databases:

generating an additional similarity score between the representation of the query mass spectrum and the individual representation of the reference mass spectrum, wherein the individual representation of the reference mass spectrum corresponds to the representative spectrum of an individual cluster of the plurality of clusters, responsive to determining that the additional similarity score exceeds a predetermined threshold value, and without utilizing a molecular identity of a molecule represented by the reference mass spectrum, retrieving metadata associated with the reference mass spectrum, deriving context information from the retrieved metadata, and adding the context information to consensus metadata associated with the query mass spectrum, wherein the context information indicates a source of the reference mass spectrum; and generating user interface data that corresponds to a user interface that includes a navigable molecular network, the molecular network include a plurality of connected nodes with individual nodes of the plurality of connected nodes corresponding to at least one molecule that is matched with one or more reference spectra, and wherein the individual nodes are selectable to display at least a portion of context information for the at least one molecule of the individual node.

* * * * *